US 009321890B2

(12) United States Patent
Tamiya et al.

(10) Patent No.: US 9,321,890 B2
(45) Date of Patent: Apr. 26, 2016

(54) MACROINITIATOR CONTAINING HYDROPHOBIC SEGMENT

(71) Applicant: Johnson & Johnson Vision Care, Inc., Jacksonville, FL (US)

(72) Inventors: Ryuta Tamiya, Shiga (JP); Kazuhiko Fujisawa, Shiga (JP); Masataka Nakamura, Shiga (JP)

(73) Assignee: Johnson & Johnson Vision Care, Inc., Jacksonville, FL (US)

( * ) Notice: Subject to any disclaimer, the term of this patent is extended or adjusted under 35 U.S.C. 154(b) by 0 days.

(21) Appl. No.: 14/301,584

(22) Filed: Jun. 11, 2014

(65) Prior Publication Data

US 2014/0296368 A1    Oct. 2, 2014

Related U.S. Application Data

(62) Division of application No. 13/449,412, filed on Apr. 18, 2012, now abandoned.

(60) Provisional application No. 61/482,260, filed on May 4, 2011.

(51) Int. Cl.
*G02B 1/10* (2015.01)
*C08G 77/452* (2006.01)
*C08G 77/26* (2006.01)
*C08G 77/388* (2006.01)
*C08L 83/08* (2006.01)
*G02B 1/04* (2006.01)
*A61L 27/18* (2006.01)
*A61L 12/14* (2006.01)

(52) U.S. Cl.
CPC ............... *C08G 77/452* (2013.01); *A61L 27/18* (2013.01); *C08G 77/26* (2013.01); *C08G 77/388* (2013.01); *C08L 83/08* (2013.01); *G02B 1/043* (2013.01); *A61L 12/14* (2013.01); *A61L 2430/16* (2013.01)

(58) Field of Classification Search
CPC .................................. G02B 1/043; A61L 12/14
See application file for complete search history.

(56) References Cited

U.S. PATENT DOCUMENTS

| 5,034,461 | A | 7/1991 | Lai et al. |
| 5,260,000 | A | 11/1993 | Nandu et al. |
| 5,760,100 | A | 6/1998 | Nicolson et al. |
| 6,637,929 | B2 | 10/2003 | Baron |
| 6,641,805 | B1 | 11/2003 | Morita et al. |
| 6,867,245 | B2 | 3/2005 | Iwata et al. |
| 7,247,692 | B2 * | 7/2007 | Laredo .......................... 526/279 |
| 7,553,880 | B2 | 6/2009 | Nicolson et al. |
| 2009/0173044 | A1 | 7/2009 | Linhardt et al. |
| 2011/0275734 | A1 | 11/2011 | Scales et al. |

FOREIGN PATENT DOCUMENTS

| CN | 101065157 A | 10/2007 |
| WO | 03022321 A2 | 3/2003 |
| WO | 03022322 A2 | 3/2003 |
| WO | 2006039467 A2 | 4/2006 |
| WO | 2008061992 A2 | 5/2008 |
| WO | 2008112874 A1 | 9/2008 |

OTHER PUBLICATIONS

PCT International Preliminary Report on Patentability, dated Nov. 5, 2013, for PCT Int'l Appln. No. PCT/US2012/035721.
PCT International Search Report, dated Jul. 16, 2012, for PCT Int'l Appln. No. PCT/US2012/035721.

* cited by examiner

*Primary Examiner* — Margaret Moore
(74) *Attorney, Agent, or Firm* — Karen A. Harding

(57) ABSTRACT

The present invention relates to macroinitiators comprising at least one hydrophobic segments in a molecule, wherein a molecular weight of the hydrophobic segment is 300 to 1800. The present invention further relates to block copolymers, wetting agent and polymeric materials having the block copolymers of the present invention associated with, which is suitable for medical devices, particularly for ophthalmic devices, including contact lenses, ophthalmic lenses, punctal plugs and artificial corneas.

18 Claims, No Drawings

MACROINITIATOR CONTAINING HYDROPHOBIC SEGMENT

RELATED APPLICATIONS

This application is a division of U.S. patent application Ser. No. 13/449,412 filed Apr. 18, 2012; which claims priority to U.S. Provisional Patent Application No. 61/482,260, filed on May 4, 2011 entitled MACROINITIATOR CONTAINING HYDROPHOBIC SEGMENT, the contents of which are incorporated by reference.

FIELD OF THE INVENTION

The present invention relates to macroinitiators useful for forming block copolymers. The present invention further relates to block copolymers, wetting agents and polymeric materials, as well as, medical devices incorporating the polymeric materials having the block copolymers of the present invention.

DESCRIPTION OF THE RELATED ART

Various compounds have been disclosed as suitable for treating preformed silicone hydrogel contact lenses including surface active segmented block copolymers, substantially water-soluble silicone-containing surfactants, functionalized hybrid PDMS/polar amphipathic compolymer block systems, including polydimethylsiloxane-PVP block copolymers and (meth)acrylated polyvinylpyrrolidone. WO2006/039467 discloses a block copolymer obtained by polymerizing a hydrophilic monomer using a hydrophobic macro azoinitiator, including VPS 0501 and VPS 1001 siloxane containing macro azoinitiators of which the siloxane units have molecular weights of 5,000 and 10,000. WO2006/039467 discloses that the block copolymers disclosed therein may be incorporated into the reaction mixtures and polymerized therewith to form medical devices having improved characteristics, including wettability.

WO2008/112874 similarly discloses that a block copolymer obtained by polymerizing a hydrophilic monomer using a hydrophobic macro azoinitiator can be used as a lens care component for contact lenses. No details are provided relating to the size of the macro azoinitiator or the process for making same. No properties are provided for the solution.

However, large polysiloxane segments can be difficult to solubilize in aqueous solutions, such as contact lens packaging, cleaning and care solutions. This can result in cloudy solutions which do not impart the desired improvement in wettability to the articles being treated. Thus there remains a need for methods for improving the properties of contact lenses and particularly silicone hydrogel contact lenses.

SUMMARY OF THE INVENTION

The present invention relates to macroinitiators comprising at least one hydrophobic segment in a molecule, wherein the molecular weight of the hydrophobic segments is 300 to 1800.

DETAILED DESCRIPTION OF THE INVENTION

As used herein "non-reactive" means incapable of forming significant covalent bonding. The absence of significant covalent bonding means that while a minor degree of covalent bonding may be present, it is incidental to the retention of the block copolymer in the polymeric article. Whatever incidental covalent bonding may be present, it would not by itself be sufficient to maintain the association of the non-reactive block copolymers with or in the polymer matrix. Instead, the vastly predominating effect keeping the block copolymers associated with the polymeric article is entrapment of at least a portion of the hydrophobic segment. The hydrophobic segment is "entrapped", according to this specification, when it is physically retained within or anchored to the polymer matrix. This is done via entanglement of the hydrophobic segment within the polymer matrix, van der Waals forces, dipole-dipole interactions, electrostatic attraction, hydrogen bonding and combinations of these effects. In one embodiment, non-reactive components are free from free radical reactive groups.

As used herein "segment" means a residue which has a structure comprising repeating units.

The present invention provides a block copolymer formed from the reaction of at least one hydrophilic monomer and a macro initiator with a hydrophobic segment having a molecular weight between about 300 and about 1800. If the molecular weight of the hydrophobic segment has a molecular weight distribution, the molecular weight is weight-average molecular weight.

The macro initiator may be obtained by reacting an azo-type initiator with a compound having the desired hydrophobic segment.

Azo-type initiators are known in the art and include aliphatic azo containing initiators, including one or more of the following compounds: 4,4'-azobis(4-cyanovalearic acid) and its derivatives, 2,2'-azobis[N-(2-carboxyethyl)-2-methylpropionamidine]hydrate, 2,2'-azobis{2-methyl-N-[2-(1-carboxybutyl)]propionamide}, and 2,2'-azobis[2-methyl-N-(2-carboxyethyl)propionamide] and the like. In one embodiment the azo-type initiator is 4,4'-azobis(4-cyanovalearic acid).

Hydrophobic segments of the present invention are those which do not yield a clear single phase when mixed with water at 2000 ppm at 25° C. When making this measurement, each end of the hydrophobic segment may be independently substituted with a hydrogen atom or an initiator residue. Examples of suitable hydrophobic segments are polysiloxanes, $C_8$-$C_{50}$ alkylene or (poly)arylene groups, hydrophobic polymers formed from monomers selected from the group consisting of $C_1$-$C_{20}$ alkyl or $C_6$-$C_{20}$ aryl (meth)acrylate monomoers such as methyl (meth)acrylate, ethyl (meth)acrylate, n-propyl (meth)acrylate, isopropyl (meth)acrylate, n-butyl (meth)acrylate, n-decyl (meth)acrylate, n-dodecyl (meth)acrylate, phenyl (meth)acrylate, and naphthyl (meth)acrylate; and silicone (meth)acrylate monomers such as 3-(meth)acryloxypropyltris(trimethylsiloxy)silane, pentamethyldisiloxanylmethyl (meth)acrylate, methyldi(trimethylsiloxy)(meth)acryloxymethylsilane, mono(meth)acryloxypropy terminated mono-n-butyl terminated polydimethylsiloxane, (2-methyl-)$_2$-propenoic acid, 2-hydroxy-3-[3[1,3,3,3-tetramethyl-1-[trimethylsilyl)oxy]disiloxanyl]propoxy]propyl ester, and 9-n-butyl-1-[3-(3-(meth)acryloyloxy-2-hydroxypropoxy)propyl]-1,1,3,3,5,5,7,7,9,9-decamethylpentasiloxane; and vinyl or allyl silicone monomers such as 3-[tris(trimethylsiloxy)silyl]propyl allyl carbamate, 3-[tris(trimethylsiloxy)silyl]propyl vinyl carbamate, trimethylsilylethyl vinyl carbonate, trimethylsilylmethyl vinyl carbonate; and aromatic vinyl monomers such as styrene, and vinylpyridine; and combinations thereof. In one embodiment the hydrophobic segment of the block copolymer is a polysiloxane segment. The polysiloxane segment may comprise $C_1$-$C_4$ polyalkyl and polyaryl substituted siloxane repeating units. Examples of suitable polysiloxane repeating units include polydimethylsiloxane, polydiethylsiloxane, polydiphenylsiloxanes and copolymers thereof. In one embodiment the polysiloxane segment is terminated on one end with an alkyl group, and in another embodiment a $C_{1-4}$ alkyl and in another methyl or n-butyl.

The hydrophobic segment of the block copolymer of the present invention has affinity towards polymeric articles formed from hydrophobic components, such as, but not limited to silicone containing articles, such as, in one embodiment, silicone elastomer lenses and silicone hydrogel contact lenses.

The present invention further relates to a wetting agent for polymeric articles comprising at least partially hydrophobic polymers, such as silicone elastomer, silicone hydrogel and PMMA contact lenses. The block copolymers formed from the macroinitiators of the present invention may, in one embodiment be incorporated into packaging solutions, storage solutions and multipurpose solutions containing the block copolymers formed via the present invention. These solutions can provide improved wettability to the polymeric article without performing a surface treatment.

In one embodiment, the hydrophobic segment-containing macroinitiators comprise one or two hydrophobic segments, each having a molecular weight of about 300 to about 1800. In another embodiment, the hydrophobic segment-containing macroinitiators comprise two hydrophobic segments because block copolymers only are obtained from the macroinitiators, while a mixture of block copolymers and hydrophilic polymers are obtained from macroinitiators comprising one hydrophobic segment. The hydrophobic segment may be formed from monomers which will associate, on a "like prefers like" basis with at least a part of the hydrophobic network of a polymeric article. For example, in one embodiment where the article is an ophthalmic device such as a PMMA, siloxane elastomer or silicone hydrogel contact lens, or a silicone elastomer punctal plug, the hydrophobic segment is a segment comprising polysiloxane.

The hydrophobic-containing macroinitiator may be formed by reacting a reactive linear polysiloxane having a functional group such as a hydroxyl group, amino group, thiol group or the like on at least one terminus with an azo-type initiator having a carboxy group.

The reactive linear polysiloxane may be selected from compounds of the formula:

Formula XI

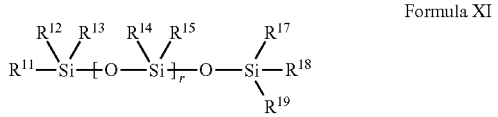

Wherein $R^{11}$ is selected from substituted and unsubstituted $C_{1-24}$ alkyl; in some embodiments substituted and unsubstituted $C_{1-10}$ alkyl and in other embodiments unsubstituted $C_{1-4}$ alkyl, and in other embodiments methyl or n-butyl;

$R^{12}$-$R^{15}$ are independently selected from $C_1$-$C_4$ alkyl and $C_{6-10}$ aryl;

r is 5-60, 6-50, 6-20, 6-15 and in some embodiments 6-12, and $R^{17}$, $R^{18}$ and $R^{19}$ are independently selected from H, unsubstituted $C_{1-4}$ alkyl, $C_{1-4}$ alkyl substituted with hydroxyl, amino and the like and combinations thereof, with the proviso that at least one of $R^{17}$, $R^{18}$ and $R^{19}$ is a hydrogen atom or comprise a hydroxyl group, amino group or thiol group.

The molecular weight of the reactive linear polysiloxane is between about 300 to about 1800, and in some embodiments between about 400 to about 1500, about 500 to about 1500, and between about 800 to about 1200.

Specific examples of reactive linear polysiloxanes include

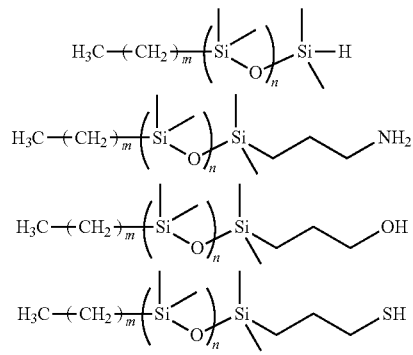

Wherein m is 0 to 3, and n is r+1 and r is as defined above.

The reactive linear polysiloxane is reacted with an azo-type initiator having a carboxy group or a vinyl group. Suitable azo-type initiators include 4,4'-azobis(4-cyanovalearic acid) and its derivatives, 2,2'-azobis[N-(2-carboxyethyl)-2-methylpropionamidine]hydrate, 2,2'-azobis{2-methyl-N-[2-(1-carboxybutyl)]propionamide}, and 2,2'-azobis[2-methyl-N-(2-carboxyethyl)propionamide] and the like. In one embodiment the azo-type initiator is 4,4'-azobis(4-cyanovalearic acid).

Generally it is desirable to control the ratio of reactive linear polysiloxane to azo-type initiator in the reaction. If the siloxane/initiator molar ratio is too high, siloxane raw material will remain after reaction, and purifying will be difficult, but if the ratio is too low (too much initiator), the yield will be reduced. Therefore ratios of 1 to 2.4, 1.3 to 2.0 and in some embodiments 1.4 to 1.9 are desirable.

The azo-type initiator and reactive linear polysiloxane are reacted via a condensation reaction or a hydrosilylation reaction at a sufficiently low temperature that the azo type initiator does not generate radicals. If the reaction temperature is too high, radicals will be generated from the azo type initiator, but if the temperature is too low, a long time will be required until the reaction is complete. Therefore the reaction temperature is preferably from −20° C. to 50° C., more preferably from 0° C. to 40° C., and most preferably from 10° C. to 35° C.

A condensation agent may also be included. Examples of condensation agents include dicyclohexyl carbodiimide (DCC), diisopropyl carbodiimide (DIPC), and N-ethyl-N'-3-dimethyl aminopropyl carbodiimide (EDC=WSCI), as well as hydrochloride salts (WSCI.HCl). A combination of DCC or WSCI and N-hydroxy succinimide (HONSu), 1-hydroxy benzotriazole (HOBt), or 3-hydroxy-4-oxo-3,4-dihydro-1,2,3-benzotriazine (HOBt) and the like can also be used. If the amount used is too low, raw material will remain and purifying will be difficult, but if the amount is too high, the condensation agent will remain and purifying will be difficult. Therefore, the molar ratio added is preferably 1.8 to 4.0 times the amount of azo type initiator having a carboxyl group, and the molar ratio is more preferably 2.0 to 3.0 times, and most preferably 2.1 to 2.7 times.

A catalyst can be added during the macro initiator synthesis reaction of the present invention in order to enhance reactivity. Suitable catalysts include nucleophilic catalysts such as, 4-dimethyl amino pyridine and the like. If the amount used is too low, much time will be required for the reaction, but if the amount is too high, removing the catalyst after the reaction will be difficult. Therefore molar ratios of catalyst to initiator of about 0.01 to about 4.0, about 0.05 to about 3.0 are desirable. In some embodiments, in order to prevent raw material from remaining, a molar ratio of catalyst to initiator about 1.0 to about 2.7 are preferred.

In one embodiment, the hydrophobic segment containing macroinitiators of the present invention have the formula:

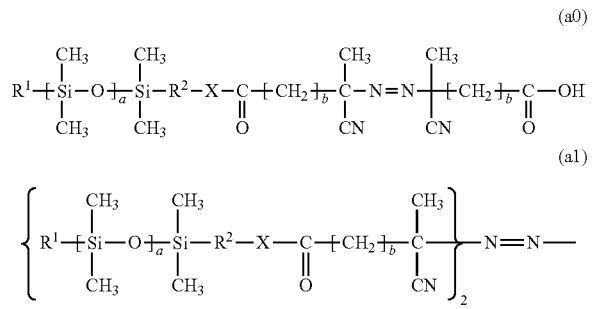

wherein in (a0) and (a1), $R^1$ is one type of group selected from an alkyl group or an alkoxy group;

$R^2$ is one type of group selected from $(CH_2)_n$ and $(CH_2)_m$—$O(CH_2)_n$;

m and n are independent, ranging from 1 to 16, more preferably from 2 to 10, most preferably from 2 to 5;

a is from 4 to 19, more preferably from 6 to 17, and most preferably from 8 to 15;

b is from 1 to 6, more preferably from 2 to 4; and

X is one type of group selected from O, NH, and S, more preferably O, and NH from the viewpoint of high reactivity, and most preferably O from the viewpoint of less byproduct.

The hydrophobic segment containing macroinitiators of the present invention are reacted with at least one hydrophilic monomer to form the block copolymers of the present invention. In one embodiment the hydrophilic segment may be formed from known hydrophilic monomers. Hydrophilic monomers are those which yield a clear single phase when mixed with water at 25° C. at a concentration of 10 wt %. Examples of hydrophilic monomers include vinyl amides, vinylimides, vinyl lactams, hydrophilic (meth)acrylates, (meth)acrylamides, styrenics, vinyl ethers, vinyl carbonates, vinyl carbamates, vinyl ureas and mixtures thereof.

Examples of suitable hydrophilic monomers include N-vinyl pyrrolidone, N-vinyl-2-piperidone, N-vinyl-2-caprolactam, N-vinyl-3-methyl-2-caprolactam, N-vinyl-3-methyl-2-piperidone, N-vinyl-4-methyl-2-piperidone, N-vinyl-4-methyl-2-caprolactam, N-vinyl-3-ethyl-2-pyrrolidone, N-vinyl-4,5-dimethyl-2-pyrrolidone, vinylimidazole, N—N-dimethylacrylamide, acrylamide, N,N-bis(2-hydroxyethyl) acrylamide, acrylonitrile, N-isopropyl acrylamide, vinyl acetate, (meth)acrylic acid, polyethylene glycol (meth)acrylates, 2-ethyl oxazoline, N-(2-hydroxypropyl)(meth)acrylamide, N-(2-hydroxyethyl)(meth)acrylamide, 2-methacryloyloxyethyl phosphorylcholine, 3-(dimethyl(4-vinylbenzyl) ammonio)propane-1-sulfonate (DMVBAPS), 3-((3-acrylamidopropyl)dimethylammonio)propane-1-sulfonate (AMPDAPS), 3-((3-methacrylamidopropyl)dimethylammonio)propane-1-sulfonate (MAMPDAPS), 3-((3-(acryloyloxy)propyl)dimethylammonio)propane-1-sulfonate (APDAPS), 3-((3-(methacryloyloxy)propyl)dimethylammonio) propane-1-sulfonate (MAPDAPS), N-vinyl-N-methylacetamide, N-vinylacetamide, N-vinyl-N-methylpropionamide, N-vinyl-N-methyl-2-methylpropionamide, N-vinyl-2-methylpropionamide, N-vinyl-N,N'-dimethylurea, and the like, and mixtures thereof. In one embodiment the hydrophilic monomer comprises N-vinyl pyrrolidone, N-vinyl-N-methylacetamide, 2-methacryloyloxyethyl phosphorylcholine, (meth)acrylic acid, N,N dimethylacrylamide and the like and mixtures thereof. In some embodiments the hydrophilic segment may also comprise charged monomers including but not limited to methacrylic acid, acrylic acid, 3-acrylamidopropionic acid, 4-acrylamidobutanoic acid, 5-acrylamidopentanoic acid, 3-acrylamido-3-methylbutanoic acid (AMBA), N-vinyloxycarbonyl-α-alanine, N-vinyloxycarbonyl-β-alanine (VINAL), 2-vinyl-4,4-dimethyl-2-oxazolin-5-one (VDMO), reactive sulfonate salts, including, sodium-2-(acrylamido)-2-methylpropane sulphonate (AMPS), 3-sulphopropyl (meth) acrylate potassium salt, 3-sulphopropyl (meth)acrylate sodium salt, bis 3-sulphopropyl itaconate di sodium, bis 3-sulphopropyl itaconate di potassium, vinyl sulphonate sodium salt, vinyl sulphonate salt, styrene sulfonate, sulfoethyl methacrylate, combinations thereof and the like. In embodiments where the hydrophilic segment comprises at least one charged hydrophilic monomer it may be desirable to include non-charged hydrophilic monomers as comonomers.

In another embodiment the hydrophilic segment is made from a hydrophilic polymer selected from a group consisting of poly-N-vinyl-2-pyrrolidone, poly-N-vinyl-2-piperidone, poly-N-vinyl-2-caprolactam, poly-N-vinyl-3-methyl-2-caprolactam, poly-N-vinyl-3-methyl-2-piperidone, poly-N-vinyl-4-methyl-2-piperidone, poly-N-vinyl-4-methyl-2-caprolactam, poly-N-vinyl-3-ethyl-2-pyrrolidone, poly-N-vinyl-4,5-dimethyl-2-pyrrolidone, polyvinyl imidazole, poly-N—N-dimethyl acrylamide, poly-N-vinyl-N-methyl acetamide, polyvinyl alcohol, polyacrylic acid, polymethacrylic acid, and poly(hydroxyethyl methacrylate), as well as blends and copolymers thereof. In another embodiment the hydrophilic segment comprises a hydrophilic polymer selected from a group consisting of poly-N-vinyl-2-pyrrolidone, poly-N—N-dimethyl acrylamide, poly-N-vinyl-N-methyl acetamide, polyvinyl alcohol, polyacrylic acid, polymethacrylic acid, and poly(hydroxyethyl methacrylate) and copolymers comprising them.

The hydrophilic monomer should be present in a concentration sufficient to achieve the desired degree of polymerization of the hydrophilic segment. If the concentration of hydrophilic monomer is too high, high viscosity will occur during polymerization, and mixing will be difficult, and in some cases impossible. Therefore a weight percentage of 10 to 60 weight % is preferable, and 15 to 50 weight % is most preferable.

If the monomer/initiator ratio is too low, gelling will readily occur during polymerization, but if the ratio is too high, polymerization will not start. Therefore, a ratio of 500 to 10,000 is preferable, 800 to 7000 is more preferable, and 1500 to 5000 is most preferable.

The polymerization may be carried out neat or with a solvent. Suitable solvents include ethers, esters, amides, aromatic and aliphatic hydrocarbons, alcohols, ketone solvents, ester solvents, ether solvents, sulfoxide solvents, amide solvents, and glycol solvents and halohydrocarbons. Among these, from the viewpoint of hard to inhibit radical polymerization, more preferable are water, and alcohol solvents, and most preferable are water and tertiary alcohol solvents. Example include t-amyl alcohol, diethyl ether, tetrahydrofuran, hexanes, methylene chloride, ethyl acetate, dimethyl formamide, water, methanol, ethanol, propanol, 2-propanol, butanol, tert-butanol, 3-methyl-3-pentanol, 3,7-dimethyl-3-octanol, benzene, toluene, xylene, hexane, heptane, octane, decane, petroleum ether, kerosene, ligroin, paraffin, acetone, methyl ethyl ketone and methyl isobutyl ketone, ethyl acetate, butyl acetate, methyl benzoate, dioctyl phthalate, ethylene glycol diacetate, diethyl ether, tetrahydrofuran, dioxane, dimethyl sulfoxide, N,N-dimethylformamide, N,N-dimethylacetamide, ethylene glycol dialkyl ether, diethylene glycol dialkyl ether, triethylene glycol dialkyl ether, tetraethylene glycol dialkyl ether, polyethylene glycol dialkyl ether, polyethylene glycol-polypropylene glycol block copolymer, and polyethylene glycol-polypropylene glycol random copolymer, and mixtures thereof and the like. Among these, from the viewpoint of hard to inhibit radical polymerization, more preferable are water, tert-butanol, tert-amyl alcohol, 3-methyl-3-pentanol and 3,7-dimethyl-3-octanol. If a solvent is used it is present in amounts between about 40 to about 90% and in some embodiments between about 50 and about 85%.

Any temperature where the selected initiator is active, and between the freezing and boiling point of the reaction components (including solvent, if used) may be used. If the temperature is too high, the polymer solution may also heat excessively and become difficult to control or dangerous. Temperature ranges between the 10 hour half-life temperature of the polymerization initiator (hereinafter referred to as T) and T+50° C., and in some embodiments between T and T+30° C. are suitable.

Suitable reaction times include up to about 72 hours and in some embodiments from about 1 to about 24 hours and in other embodiments from about 2 to about 10 hours.

The resulting block copolymer may purified via distillation, column chromatography, precipitation, washing off impurities by solvent which the block copolymer is insoluble to, fractionation by GPC, or any other traditional means of polymer isolation.

The block copolymer may be expressed by formula (b1) or (b2).
Formula:

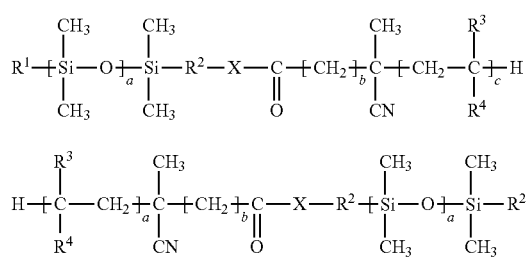

The block copolymers of the present invention have average molecular weights from about 10,000 to about 3,000,000 more preferably from about 50,000 to about 1,000,000, and most preferably from about 100,000 to about 600,000. If the average molecular weight is too low, the block copolymers will not provide enough wettability. However, if the average molecular weight is too high, the viscosity of the block copolymer solution is too high. In another embodiment, the block copolymers of the invention further comprising about 0.01 to about 5 weight % of at least one hydrophobic segment and about 95 to about 99.99 weight % of a hydrophilic segment, more preferably approximately 0.05 to approximately 3 weight % of a hydrophobic segment and approximately 97 to approximately 99.95 weight % of a hydrophilic segment, and most preferably approximately 0.1 to approximately 1 weight % of a hydrophobic segment and approximately 99 to approximately 99.9 weight % of a hydrophilic segment.

In some embodiments the block copolymer contains approximately 0.01 to approximately 5 weight % of a hydrophobic segment and approximately 95 to approximately 99.9 weight % of a hydrophilic segment.

If the silicone (PDMS) block in the block copolymer is too large, even though the block copolymer overall is hydrophilic due to the degree of polymerization of the hydrophilic monomer, the overall solubility of the block copolymer will be insufficient. However, if the silicone segment is too small the (wherein in (b1) and (b2), $R^1$ is one type of group selected from an alkyl group or an alkoxy group;

$R^2$ is one type of group selected from $(CH_2)_n$ or $(CH_2)_m—O(CH_2)_n$;

m and n are independent, ranging from 1 to 16, more preferably from 2 to 10, most preferably from 2 to 5;

a is from 4 to 19, more preferably from 6 to 17, and most preferably from 8 to 15;

b is from 1 to 6, more preferably from 2 to 4, c is from 1 to 10,000, more preferably from 100 to 8000, and most preferably from 1000 to 6000, X is one type of group selected from O, NH, and S, more preferably O, and NH from the viewpoint of high reactivity, and most preferably O from the viewpoint of less byproduct; and $R^3$ and $R^4$ represent groups made of monomers with hydrophilicity wherein a monomer is expressed by general formula (n)).

block copolymer will not persistently associate with the polymeric article and will not provide the desired benefit over the useful life of the article.

The block copolymers of the present invention are non-reactive. The present invention further relates to polymeric materials, and in some embodiments medical devices formed from polymeric materials have the block copolymers of the present invention associated therewith.

Suitable medical devices include ophthalmic lenses, endoscopes, catheters, transfusion tubes, gas transport tubes, stents, sheaths, cuffs, tube connectors, access ports, drainage bags, blood circuits, wound covering material, implants and various types of medicine carriers, but is particularly suitable for ophthalmic devices, including contact lenses, ophthalmic lenses, punctal plugs and artificial corneas.

Where the medical device is an ophthalmic device it may be a contact lens, corneal implant, punctal plug or the like.

Suitable silicone hydrogel materials are known and may be used, including but not limited to senofilcon, galyfilcon, lotrafilcon A and lotrafilcon B, balafilcon, comfilcon and the like. Almost any silicone hydrogel polymer can be treated using the hydrophilic polymers of the present invention, including but not limited to those disclosed in U.S. Pat. No. 6,637,929, WO03/022321, WO03/022322, U.S. Pat. No. 5,260,000, U.S. Pat. No. 5,034,461, U.S. Pat. No. 6,867,245, WO2008/061992, U.S. Pat. No. 5,760,100, U.S. Pat. No. 7,553,880.

The present invention further relates to optically clear, aqueous solutions comprising at least one block copolymer of the present invention in an amount sufficient to reduce at least one of contact angle, lipid uptake or protein uptake. Suitable amounts include up to about 5000 ppm, about 50 to about 3000 ppm and about 100 to about 2000 ppm. The block copolymer may be incorporated into said polymeric article in amounts from about 0.1 ppm to about 30% of the block copolymer more preferably from about 1000 ppm to about 25%, and most preferably from about 1% to about 20%.

The hydrophilic polymers of the present invention may be non-covalently associated with a variety of polymers including polysiloxanes, silicone hydrogels, polymethyl methacrylate, polyethylene, polypropylene, polycarbonate, polyethylene terapthalate, polytetrafluoroethylene, and mixtures thereof and the like. In this embodiment it is believed that the terminal polysiloxane associates with the substrate which comprises hydrophobic polymer components. In this embodiment the block copolymer is dissolved in a solvent which also swells the substrate. The polymer substrate is contacted with the solution comprising the block copolymer. When the substrate is a silicone hydrogel article, such as a contact lens, suitable solvents include packing solution, storing solution and cleaning solutions. Using this embodiment as an example, the silicone hydrogel lens is placed in a packing solution comprising the block copolymer. The hydrophilic polymer is present in the solution in amounts between about 0.001 and about 10%, in some embodiments between about 0.005 and about 2% and in other embodiments between about 0.01 and about 0.5 weight %, based upon all components in the solution.

The packing solutions of the invention may be any water-based solution that is used for the storage of contact lenses. Typical solutions include, without limitation, saline solutions, other buffered solutions, and deionized water. The preferred aqueous solution is saline solution containing salts including, without limitation, sodium chloride, sodium borate, sodium phosphate, sodium hydrogenphosphate, sodium dihydrogenphosphate, or the corresponding potassium salts of the same. These ingredients are generally combined to form buffered solutions that include an acid and its conjugate base, so that addition of acids and bases cause only a relatively small change in pH. The buffered solutions may additionally include 2-(N-morpholino)ethanesulfonic acid (MES), sodium hydroxide, 2,2-bis(hydroxymethyl)-2,2',2"-nitrilotriethanol, N-tris(hydroxymethyl)methyl-2-aminoethanesulfonic acid, citric acid, sodium citrate, sodium carbonate, sodium bicarbonate, acetic acid, sodium acetate, ethylenediamine tetraacetic acid and the like and combinations thereof. Preferably, the solution is a borate buffered or phosphate buffered saline solution. The solutions may also include known additional components such as viscosity adjusting agents, antimicrobial agents, polyelectrolytes, stabilizers, chelants, antioxidants, combinations thereof and the like.

The substrate is contacted with the block copolymer under conditions sufficient to incorporate a lubricious and surface-wetting effective amount of the block copolymer. As used herein, a lubricious effective amount, is an amount necessary to impart a level of lubricity which may be felt manually (such as by rubbing the device between one's fingers) or when the device is used. Additionally, as used herein, a surface-wetting effective amount is an amount necessary to impart a level of increased wetability to the lens, as determined via known contact angle measurement techniques (i.e. sessile drop, captive bubble, or dynamic contact angle measurements). It has been found that in one embodiment, where the device is a soft contact lens, amounts of hydrophilic polymer as little as 50 ppm provide improved lens "feel" and lowered surface contact angles, as measured by sessile drop. Amounts of block copolymer greater than about 50 ppm, and more preferably amounts greater than about 100 ppm, (measured via extraction in 2 ml of a 1:1 DMF:deionized water solution, for 72 hours) add a more pronounced improvement in feel. Thus, in this embodiment, the block copolymer may included in a solution in concentrations up to about 5000 ppm, in some embodiments between about 10 and 3000 ppm, and in some embodiments between about 10 and about 2000 ppm. The packaged lens may be heat treated to increase the amount of hydrophilic polymer which permeates and becomes entangled in the lens. Suitable heat treatments, include, but are not limited to conventional heat sterilization cycles, which include temperatures of about 120° C. for times of about 20 minutes and may be conducted in an autoclave. If heat sterilization is not used, the packaged lens may be separately heat treated. Suitable temperatures for separate heat treatment include at least about 40° C., and preferably between about 50° C. and the boiling point of the solution. Suitable heat treatment times include at least about 10 minutes. It will be appreciated that higher temperatures will require less treatment time.

In one embodiment, the polymeric article is formed from a reactive mixture comprising a silicone monomer comprising a hydroxyl group.

Treatment of the polymeric article with the block copolymer can be performed on the entire polymer or can be performed only on a portion of the polymer such as only on the surface or a portion of the surface.

The present invention will be described in further detail below through the use of working examples, but the present invention is not limited to these working examples.

Analytical Methods (1) GPC Measurement

GPC measurement was performed at the following conditions.

Equipment: Tosoh Corporation
Column: TSKgel SUPER HM_H, 2 columns (particle diameter; 5 μm, 6.0 mm ID×15 cm)
Mobile phase: N-methylpyrrolidone (10 mM LiBr)
Column temperature: 40° C.
Measurement time: 40 minutes
Injection quantity: 10 μL
Detector: RI detector
Flow rate: 0.2 mL/minute
Sample concentration: 0.4 weight %
Standard sample: polystyrene (molecular weight 500 to 1.09 million)

(2) Transmission Measurement

A packaging solution made by dissolving 2000 ppm of block copolymer was placed in a quartz cell, and a transmissivity was measured using a color computer (model: SM7-CH) manufactured by Suga Test Instruments Co., Ltd.

(3) Contact Angle Measurement

Wettability of lenses was determined using a sessile drop technique measured using KRUSS DSA-100 TM instrument at room temperature and using DI water as probe solution. The lenses to be tested (3-5/sample) were rinsed in DI water to remove carry over from packing solution. Each test lens was placed "bowl side down" on the convex surface of the lens holder, ensuring proper central syringe alignment and that the syringe corresponds to the assigned liquid. Blotting paper (dry Whatman #1 filter paper on a glass sheet) is gently placed on the lens without any downward pressure for 20 seconds. A 3 to 4 microliter of DI water drop was formed on the syringe tip using DSA 100-Drop Shape Analysis software ensuring the liquid drop was hanging away from the lens. The drop was released smoothly on the lens surface by moving the needle down. The needle was withdrawn away immediately after dispensing the drop. The liquid drop was allowed to equilibrate on the lens for 5 to 10 seconds and the contact angle was computed based on the contact angle measured between the drop image and the lens surface.

(4) Lipid Uptake

A standard curve was set up for each lens type under investigation. Tagged cholesterol (cholesterol labeled with NBD ([7-nitrobenz-2-oxa-1,3-diazol-4-yl], CH-NBD; Avanti, Alabaster, Ala.)) was solubilized in a stock solution of 1 mg/mL lipid in methanol at 35° C. Aliquots were taken from this stock to make standard curves in phosphate-buffered saline (PBS) at pH 7.4 in a concentration range from 0 to 100 micg/mL.

One milliliter of standard at each concentration was placed in the well of a 24-well cell culture plate. 10 lenses of each type were placed in another 24-well plate and soaked alongside the standard curve samples in 1 mL of a concentration of 20 micg/ml of CH-NBD. Another set of lenses (5 lenses) were soaked in PBS without lipids to correct for any autofluorescence produced by the lens itself. All concentrations were made up in phosphate buffered saline (PBS) at pH 7.4. Standard curves, test plates (containing lenses soaked in CH-NBD) and control plates (containing lenses soaked in PBS) were all wrapped in aluminum foil to maintain darkness and were incubated for 24 hours, with agitation at 35.C. After 24 hours the standard curve, test plates and control plates were removed from the incubator. The standard curve plates were immediately read on a micro-plate fluorescence reader (Synergy HT)).

The lenses from the test and control plates were rinsed by dipping each individual lens 3 to 5 times in 3 consecutive vials containing approximately 100 ml of PBS to ensure that only bound lipid would be determined without lipids carryover. The lenses were then placed in a fresh 24-well plate containing 1 mL of PBS in each well and read on the fluorescence reader. After the test samples were read, the PBS was removed, and 1 mL of a fresh solution of CH-NBD were placed on the lenses in the same concentrations as previously mentioned and placed back in the incubator at 35° C., with rocking, until the next period. This procedure was repeated for 15 days until complete saturation of lipids on lenses. Only the lipid amount obtained at saturation was reported.

Working Example 1

1.68 g (6 mmol) of 4,4'-azobis(4-cyanovaleric acid) and 1.83 g (15 mmol) of 4-dimethyl amino pyridine, 3.0 g (15 mmol) of N,N-dicyclohexyl carbodiimide, and 40 mL of acetone were added to a 200 mL three mouth flask equipped with a calcium chloride tube under nitrogen gas flow. 8.58 g (9 mmol) of polydimethylsiloxane having a hydroxyl group at one end and expressed by the following formula (a2)

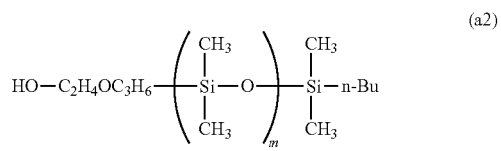

(a2)

(manufactured by Chisso Corporation FM-0411, Mw 1000) was added by drops to the solution and agitated for six hours at room temperature. A precipitated solid was filtered out, hexane was added to the filtrate obtained, and then the filtrate was washed two times with 0.5 N HCl, two times with saturated sodium bicarbonate aqueous solution, and one time with saturated sodium chloride aqueous solution. The organic phase was dried using sodium sulfate, filtered, and then concentrated to obtain crude product. The crude product was purified using a silica gel column (silica gel 180 g, hexane/ethyl acetate=100/0→10/1 (v/v), 400 mL each), and 5.18 g of the target silicone macro initiator was obtained.

Working Example 2

1.40 g (5 mmol) of 4,4'-azobis(4-cyanovaleric acid), 9.1 g (9.1 mmol) of polydimethylsiloxane having an amino group at one end and expressed by the following formula (a3) (manufactured by Chisso Corporation, FM0311, Mw 1000), 0.67 g (5.5 mmol) of 4-dimethyl aminopyridine, and 50 mL of acetone were added to a 200 mL three mouth flask equipped with a calcium chloride tube under nitrogen gas flow.

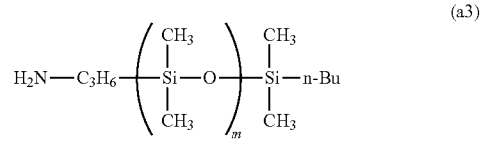

(a3)

1.70 mL (11 mmol) of N,N-diisopropyl carbodiimide was added by drops to this blended solution. After agitating for 6 hours at ambient temperature, a precipitated solid was filtered out, hexane was added to the filtrate obtained, and then the filtrate was washed two times with 0.5 N HCl, two times with saturated sodium bicarbonate aqueous solution, and one time with saturated sodium chloride aqueous solution. The organic phase was dried using sodium sulfate, filtered, concentrated, and then the crude product was purified using a silica gel column (silica gel 180 g, hexane/ethyl acetate=10/1→3/1→2/1, 300 mL each), and 1.89 g of the target silicone macro initiator was obtained.

Comparative Example 1

The silicone macro initiator wherein the molecular weight of the silicone portion is 5000 was obtained by using the same method as Working Example 1 except that the polydimethylsiloxane containing a hydroxyl group on one end (a2) was replaced a polydimethylsiloxane of the same structure, but having a higher molecular weight (manufactured by Chisso Corporation, FM-0421, Mw 5000). The resulting silicone macroinitiator was purified as described in Working Example 1.

Comparative Example 2

The silicone macro initiator wherein the molecular weight of the silicone portion is 10,000 was obtained by the same method as Working Example 1 except that the polydimethylsiloxane containing a hydroxyl group on one end (a2) was replaced a polydimethylsiloxane of the same structure, but having a higher molecular weight (manufactured by Chisso Corporation, FM-0425, Mw 10,000), and then purifying.

Working Example 3

N-vinyl pyrrolidone (NVP, 29.56 g, 0.266 mol), the silicone macro initiator expressed by the following formula (a4) obtained by working example 1 (Mw of silicone portion is 1000, 0.19 g, 0.0866 mmol), and t-amyl alcohol (TAA, 69.42 g) were added to a 200 mL three mouth flask, and then a three way cock, thermometer, and mechanical stirrer were attached.

The inside of the three mouth flask was evacuated using a vacuum pump and then substituted with argon, three times, and then the temperature was increased to 70° C. After confirming that the temperature had stabilized and heat generation was not occurring, the temperature was increased to 75° C. and the sample was agitated for 6 hours.

After polymerization was complete, the temperature was cooled to room temperature, and then the sample was poured into n-hexane/ethanol=600 mL/20 mL and allowed to sit. The supernatant fluid was removed by decanting, and then the washing was performed 2 times using n-hexane/ethanol=500 mL/20 mL. The solid fraction obtained was dried for 16 hours at 40° C. in a vacuum dryer, and then liquid nitrogen was added, the sample was crushed using a spatula, and then transferred to a bag with a zipper. Drying was performed for

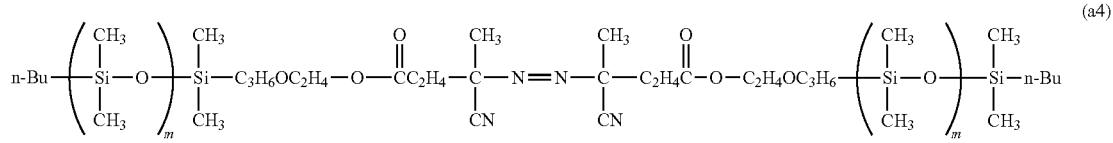

(a4)

The inside of the three mouth flask was evacuated using a vacuum pump and then substituted with argon, three times, and then the temperature was increased to 70° C. After confirming that the temperature had stabilized and heat generation was not occurring, the temperature was increased to 75° C. and the sample was agitated for 6 hours.

After polymerization was complete, the temperature was cooled to room temperature, and then the sample was poured into n-hexane/ethanol=500 mL/40 mL and allowed to sit. The supernatant fluid was removed by decanting, and then the washing was performed 2 times using n-hexane/ethanol=500 mL/20 mL. The solid fraction obtained was dried for 16 hours at 40° C. in a vacuum dryer, and then liquid nitrogen was added, the sample was crushed using a spatula, and then transferred to a bag with a zipper. Drying was performed for 3 hours at 40° C. using a vacuum dryer to obtain a block copolymer. The molecular weight of the block copolymer obtained was as shown in Table 1.

Working Examples 4 Through 10

Additional block copolymers were formed according to the procedure of Working Example 3, but with the components in the amounts indicated in Table 1. The molecular weight of the block copolymer obtained was as shown in Table 1.

Working Example 11

N-vinyl pyrrolidone (NVP, 31.12 g, 0.28 mol), the silicone macro initiator expressed by the following formula (a5) obtained by Working Example 1 (Mw of silicone portion is 1000, 0.15 g, 0.07 mmol), and t-amyl alcohol (TAA, 72.96 g) were added to a 200 mL three mouth flask, and then a three way cock, thermometer, and mechanical stirrer were attached.

3 hours at 40° C. using a vacuum dryer to obtain a block copolymer. The molecular weight of the block copolymer obtained was as shown in Table 1.

Working Examples 12 Through 13

Additional block copolymers were formed according to the procedure of Working Example 11, but with the components in the amounts indicated in Table 1. The molecular weight of the block copolymer obtained was as shown in Table 1.

Comparative Example 3

Polymerization was performed by the same method as Working Example 3, except that the polymerization initiator was substituted with the silicone macroinitiator of Comparative Example 1 (molecular weight (Mw) of the silicone portion 5000), and the amounts of the components used were as indicated in Table 1. The molecular weight of the block copolymer obtained was as shown in Table 1.

Comparative Example 4 and 5

Polymerization was performed by the same method as Working Example 3, except that the polymerization initiator was substituted with a silicone macroinitiator of Comparative Example 2 (molecular weight (Mw) of the silicone portion 10,000), and the amounts of the components used were as indicated in Table 1. The molecular weight of the block copolymer obtained was as shown in Table 1.

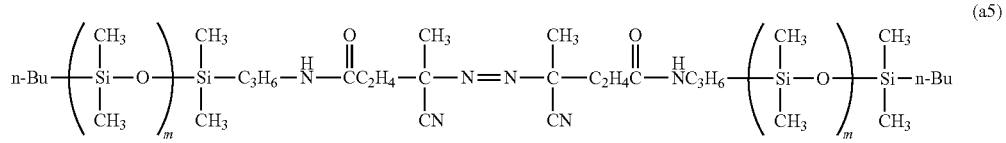

(a5)

TABLE 1

| Ex. # | NVP (g) | macro-initiator Ex# | macro-initiator (g) | TAA (g) | Mn (kD) | Mw (kD) |
|---|---|---|---|---|---|---|
| 3 | 29.56 | 1 | 0.19 | 69.42 | 113.3 | 293.9 |
| 4 | 24.62 | 1 | 0.19 | 24.81 | 132.0 | 509.0 |
| 5 | 25.9 | 1 | 0.19 | 39.15 | 148.5 | 505.0 |
| 6 | 15.54 | 1 | 0.2 | 36.9 | 48.5 | 135.4 |
| 7 | 31.07 | 1 | 0.1 | 72.73 | 78.4 | 189.2 |
| 8 | 5.18 | 1 | 0.1 | 29.92 | 42.7 | 93.8 |
| 9 | 19.45 | 1 | 0.15 | 45.73 | 88.7 | 251.6 |
| 10 | 31.10 | 1 | 0.15 | 72.92 | 70.9 | 198.1 |
| 11 | 31.12 | 2 | 0.15 | 72.96 | 80.0 | 228.8 |
| 12 | 23.34 | 2 | 0.15 | 35.24 | 103.1 | 353.7 |
| 13 | 23.34 | 2 | 0.15 | 23.49 | 114.6 | 406.8 |
| CE3 | 15.34 | CE1 | 0.46 | 36.87 | 69.9 | 183.9 |
| CE4 | 16.67 | CE2 | 1.0 | 41.23 | 68.69 | 172.39 |
| CE5 | 44.46 | CE2 | 1.0 | 106.1 | 67.96 | 166.94 |

Working Example 14

Polymerization was performed by the same method as Working Example 3, except that NVP was substituted with N,N-dimethylacrylamide (DMA), and the amounts of the components used were as indicated in Table 2. The molecular weight of the block copolymer obtained was as shown in Table 2.

Working Example 15 Through 16

Additional block copolymers were formed according to the procedure of Working Example 14, but with the components in the amounts indicated in Table 2. The molecular weight of the block copolymer obtained was as shown in Table 2.

TABLE 2

| Ex. # | DMA (g) | macro-initiator Ex# | macro-initiator (g) | TAA (g) | Mn (kD) | Mw (kD) |
|---|---|---|---|---|---|---|
| 14 | 17.4 | 1 | 0.15 | 40.8 | 222.5 | 582.8 |
| 15 | 34.7 | 1 | 0.15 | 81.3 | 263.4 | 693.3 |
| 16 | 26.4 | 1 | 0.19 | 62.0 | 204.1 | 728.4 |

Working Example 17

The block copolymers obtained by Working Examples 3 through 8 and 11 through 14, as well as comparative examples 3 through 5 were dissolved at a concentration of 2000 ppm in packaging solutions. The transmissivity of the solutions obtained was measured and are shown in Table 3.

TABLE 3

| Ex# | Silicone portion Mw | Block copolymer Mn (kD) | Block copolymer Mw (kD) | Transmissivity (%) | Transparency |
|---|---|---|---|---|---|
| 3 | 1000 | 113.3 | 293.9 | 97.37 | Transparent |
| 4 | 1000 | 132.0 | 509.0 | 96.97 | Transparent |
| 5 | 1000 | 148.5 | 505.0 | 96.38 | Transparent |
| 6 | 1000 | 48.5 | 135.4 | 97.76 | Transparent |
| 7 | 1000 | 78.4 | 189.2 | 96.74 | Transparent |
| 8 | 1000 | 42.7 | 93.8 | 93.65 | Transparent |
| 11 | 1000 | 80.0 | 228.8 | 98.57 | Transparent |
| 12 | 1000 | 103.1 | 353.7 | 98.38 | Transparent |
| 13 | 1000 | 114.6 | 406.8 | 97.30 | Transparent |
| 14 | 1000 | 204.1 | 728.4 | 97.37 | Transparent |
| CE3 | 5000 | 69.9 | 183.9 | 91.39 | White cloudy |
| CE4 | 10,000 | 68.69 | 172.39 | 78.63 | White cloudy |
| CE5 | 10,000 | 67.96 | 166.94 | 89.38 | White cloudy |

As shown in Table 3, the copolymers of Examples 3 through 8 and 11-14 all formed transparent solutions, even at 2000 ppm. When the molecular weight of the siloxane segment was above about 5000 (Comparative Examples 3 through 5) the transmissivity of the 2000 ppm solution was reduced and a clear solution could not be obtained.

Working Example 18

ACUVUE OASYS with Hydraclear Plus contact lenses (senofilcon A) were immersed in packaging solutions obtained by dissolving 2000 ppm of the block copolymers obtained in Working Examples 3, 9, and 10, and then immersing for 24 hours in a packaging solution that did not contain the block copolymer. The samples were removed and the contact angle was measured. The results are shown in Table 4. A lipid uptake test was also performed, and the results are shown in Table 4. All of the lenses were found to have reduced lipid uptake compared to the lenses which were not soaked in the block copolymers.

TABLE 4

| Copolymer Ex# | Contact angle (°) | lipid uptake (μg/lens) |
|---|---|---|
| No treatment | 53 | 28.2 |
| 3 | 38 | 14.4 |
| 9 | 69 | 14.8 |
| 10 | 57 | 15.1 |

The invention claimed is:

1. A method comprising contacting a silicone hydrogel contact lens with a packaging solution comprising a surface-wetting effective amount of at least one block copolymer comprising one hydrophilic segment and one hydrophobic segment having a weight average molecular weight of 300 to 1800, the block copolymer expressed by formula (b1) Formula:

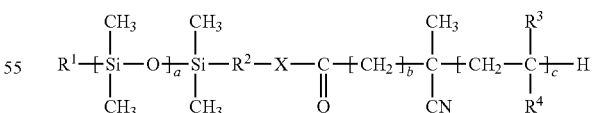

(b1)

wherein in (b1), $R^1$ is selected from the group consisting of an alkyl group and an alkoxy group;
$R^2$ is selected from the group consisting of $(CH_2)_n$ and $(CH_2)_m$—$O(CH_2)_n$;
m and n are independent, ranging from 1 to 16; a is from 4 to 19; b is from 1 to 6, c is from 1 to 10,000, X is one type of group selected from the group consisting of O, NH, and S; and $R^3$ and $R^4$ represent groups made of hydrophilic monomers expressed by general formula (n)

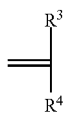

(n)

under conditions sufficient to associate said block copolymer with said contact lens.

2. The method of claim 1 wherein said surface-wetting effective amount comprises at least about 50 ppm block copolymer.

3. The method of claim 1 wherein said surface-wetting effective amount comprises at least about 10 to about 3000 ppm block copolymer.

4. The method of claim 1 wherein said surface-wetting effective amount comprises about 10 to about 2000 ppm block copolymer.

5. The method of claim 1 further wherein said contacting step further comprising heating the solution and contact lens.

6. The method of claim 5 wherein said heating step comprises at least one heat sterilization cycle.

7. The method of claim 5 wherein said heating step comprises autoclaving.

8. The method of claim 5 where said heating step is conducted at a temperature of at least about 40° C.

9. The method of claim 5 wherein said heating conducted for at least about 10 minutes.

10. The method of claim 5 wherein said block copolymer is persistently associated with said contact lens over a useful life of the contact lens.

11. The method according to any one of claims 1-10, wherein the silicone hydrogel is polymerized from a reaction mixture comprising at least one silicone monomer having a hydroxyl group.

12. The method according to claim 11, wherein an amount of component derived from a silicone monomer that is used in the silicone hydrogel is approximately 5 to approximately 95 weight %.

13. The method according to any one of claims 1-10, wherein the silicone hydrogel is polymerized from a reaction mixture comprising at least one hydrophilic monomer selected from a group consisting of N,N-dimethyl acrylamide (DMA), 2-hydroxyethyl acrylate, glycerol methacrylate, 2-hydroxyethyl methacrylate amide, polyethylene glycol mono methacrylate, methacrylic acid, acrylic acid, N-vinyl pyrrolidone, N-vinyl-N-methyl acetamide, N-vinyl-N-ethyl acetamide, N-vinyl-N-ethyl form amide, N-vinyl formamide, N-2-hydroxyethyl vinyl carbamate, N-carboxy-beta-alanine N-vinylester, reactive polyethylene polyol, hydrophilic vinyl carbonate, vinyl carbamate monomer, hydrophilic oxazolone monomer, hydrophilic oxazoline monomer, and combinations thereof.

14. The method of claim 1 wherein said block copolymer permeates into and is entangled in said silicone hydrogel.

15. The method according to claim 14, wherein said block copolymer is incorporated into an article formed from said silicone hydrogel in amounts from approximately 0.1 ppm to approximately 30 weight % of the said article.

16. The method according to any one of claims 1 through 10, wherein a weight-average molecular weight of the block copolymer is from approximately 10,000 to approximately 3,000,000.

17. The method according to any one of claims 1 through 10, wherein the block copolymer contains approximately 0.01 to approximately 5 weight % of a hydrophobic segment and approximately 95 to approximately 99.9 weight % of a hydrophilic segment.

18. The method according to any one of claims 1 through 10, wherein the hydrophilic segment is a segment made from a hydrophilic polymer selected from the group consisting of poly-N-vinyl-2-pyrrolidone, poly-N-vinyl-2-piperidone, poly-N-vinyl-2-caprolactum, poly-N-vinyl-3-methyl-2-caprolactum, poly-N-vinyl-3-methyl-2-piperidone, poly-N-vinyl-4-methyl-2-piperidone, poly-N-vinyl-4-methyl-2-caprolactum, poly-N-vinyl-3-ethyl-2-pyrrolidone, poly-N-vinyl-4,5-dimethyl-2-pyrrolidone, polyvinyl imidazole, poly-N—N-dimethyl acrylamide, poly-N-vinyl-N-methyl acetamide, polyvinyl alcohol, polyacrylic acid, polymethacrylic acid, and poly(hydroxyethyl methacrylate), as well as blends and copolymers thereof.

\* \* \* \* \*